United States Patent
Spencer et al.

(10) Patent No.: US 12,083,266 B2
(45) Date of Patent: Sep. 10, 2024

(54) POUCHES CONTAINING AN AEROSOLIZABLE MATERIAL, A CONTAINER AND AEROSOL GENERATING DEVICE FOR USE THEREWITH

(71) Applicant: NICOVENTURES TRADING LIMITED, London (GB)

(72) Inventors: Alfred Vincent Spencer, London (GB); Walid Abi Aoun, London (GB); Kevin Blick, London (GB)

(73) Assignee: NICOVENTURES TRADING LIMITED, London (GB)

( * ) Notice: Subject to any disclaimer, the term of this patent is extended or adjusted under 35 U.S.C. 154(b) by 1074 days.

(21) Appl. No.: 15/733,451

(22) PCT Filed: Feb. 1, 2019

(86) PCT No.: PCT/EP2019/052488
§ 371 (c)(1),
(2) Date: Jul. 31, 2020

(87) PCT Pub. No.: WO2019/149881
PCT Pub. Date: Aug. 8, 2019

(65) Prior Publication Data
US 2021/0100285 A1 Apr. 8, 2021

(30) Foreign Application Priority Data
Feb. 1, 2018 (GB) ...................... 1801655

(51) Int. Cl.
*A61M 15/00* (2006.01)
*A24D 1/20* (2020.01)
(Continued)

(52) U.S. Cl.
CPC .......... *A61M 15/0051* (2014.02); *A24D 1/20* (2020.01); *A24F 15/01* (2020.01); *A24F 15/18* (2013.01);
(Continued)

(58) Field of Classification Search
CPC ............ A61M 15/0051; A61M 15/009; A61M 21/02; A61M 2021/0016; A24F 40/53;
(Continued)

(56) References Cited

U.S. PATENT DOCUMENTS 3,239,117 A * 3/1966 Letchworth ........ B65D 85/8085
221/25
2017/0143042 A1 5/2017 Batista et al.
2021/0100285 A1* 4/2021 Spencer ............. B65D 83/0463

FOREIGN PATENT DOCUMENTS

DE 3844022 C1 2/1990
EP 2083643 A1 * 8/2009 ............. A24B 13/02
(Continued)

OTHER PUBLICATIONS

"International Preliminary Report on Patentability for Application No. PCT/EP2019/052488, dated Aug. 13, 2020", 8 pages.
(Continued)

*Primary Examiner* — Khiem M Nguyen
(74) *Attorney, Agent, or Firm* — Husch Blackwell LLP

(57) ABSTRACT

There is described a chain of pouches including a plurality of pouches each pouch containing aerosolizable material. Each pouch in the chain is connected to at least one other pouch in the chain by a respective weakened region. The chain is arranged to be foldable and breakable at each respective weakened region. Each pouch is porous to enable aerosol to flow through or out of the pouch.

13 Claims, 7 Drawing Sheets

(51) Int. Cl.
- *A24F 15/01* (2020.01)
- *A24F 15/18* (2006.01)
- *A24F 40/30* (2020.01)
- *A24F 40/40* (2020.01)
- *A24F 40/42* (2020.01)
- *A24F 40/53* (2020.01)
- *A61M 21/00* (2006.01)
- *A61M 21/02* (2006.01)
- *B65D 77/06* (2006.01)
- *B65D 83/04* (2006.01)
- *A24F 40/10* (2020.01)
- *A24F 40/20* (2020.01)

(52) U.S. Cl.
CPC .............. *A24F 40/30* (2020.01); *A24F 40/42* (2020.01); *A24F 40/53* (2020.01); *A61M 15/009* (2013.01); *A61M 21/02* (2013.01); *B65D 77/06* (2013.01); *B65D 83/0463* (2013.01); *A24F 40/10* (2020.01); *A24F 40/20* (2020.01); *A24F 40/40* (2020.01); *A61M 2021/0016* (2013.01)

(58) Field of Classification Search
CPC .......... A24F 40/42; A24F 40/40; A24F 40/30; A24F 40/20; A24F 40/10; A24F 15/18; A24F 15/01; A24F 15/009; A24D 1/20; B65D 77/06; B65D 83/0463
USPC .......................................................... 131/328
See application file for complete search history.

(56) References Cited

FOREIGN PATENT DOCUMENTS

| | | | | |
|---|---|---|---|---|
| RU | 2420290 | C2 | 6/2011 | |
| RU | 2480485 | C2 | 4/2013 | |
| RU | 145715 | U1 | 9/2014 | |
| RU | 158129 | U1 | 12/2015 | |
| WO | WO-2016156493 | A2 * | 10/2016 | ............... A24C 5/01 |
| WO | WO-2016162446 | A1 * | 10/2016 | ............... A24B 3/14 |

OTHER PUBLICATIONS

"International Search Report and Written Opinion received for PCT Patent Application No. PCT/EP2019/052488, dated May 3, 2019", 11 pages.

"Office Action For Russian Application No. 2020124363, dated Feb. 17, 2021", 3 pages (Official Copy Only).

\* cited by examiner

POUCHES CONTAINING AN AEROSOLIZABLE MATERIAL, A CONTAINER AND AEROSOL GENERATING DEVICE FOR USE THEREWITH

PRIORITY CLAIM

The present application is a National Phase entry of PCT Application No. PCT/EP2019/052488, filed Feb. 1, 2019, which claims priority from GB Patent Application No. 1801655.0, filed Feb. 1, 2018, each of which is hereby fully incorporated herein by reference.

TECHNICAL FIELD

The present disclosure relates to a chain of pouches containing aerosolizable material, a container for a chain of pouches containing aerosolizable material and an aerosol generating device for receiving a chain of pouches.

BACKGROUND

Articles such as cigarettes, cigars and the like burn tobacco during use to create tobacco smoke. Attempts have been made to provide alternatives to these articles, which burn tobacco, by creating products that release compounds without burning. Examples of such products are so-called heat-not-burn products, also known as tobacco heating products or tobacco heating devices, which release compounds by heating, but not burning, the material. The material may be for example tobacco or other non-tobacco products or a combination, such as a blended mix, which may or may not contain nicotine.

Inserting aerosolizable material into aerosol generating devices such as tobacco heating devices by hand can result in aerosolizable material remaining on the user after the insertion and can present general hygiene issues.

SUMMARY

According to a first aspect of the present disclosure, there is provided a chain of pouches comprising: a plurality of pouches each pouch containing aerosolizable material; and, wherein each pouch in the chain is connected to at least one other pouch in the chain by a respective weakened region, wherein the chain is arranged to be foldable and breakable at each respective weakened region, and wherein each pouch is porous to enable aerosol to flow through or out of the pouch.

Each individual pouch containing aerosolizable material may have an average pore area of about 0.03 mm$^2$ to 0.15 mm$^2$.

Each individual pouch may be made from at least one of: an aluminum mesh; filter material; food-grade plastic; silk cellulose acetate; and, polyactic acid.

Each individual pouch may contain at least about 0.1 to 250 mg of aerosolizable material.

At least one of the weakened regions may be a perforated region.

At least one of the weakened regions may be a folded region.

The aerosolizable material may be at least one of the following: tobacco; a tobacco-containing material; leaf material; herbal material; or, substances as used in aromatherapy.

According to a second aspect of the present disclosure, there is provided a container for containing a chain of pouches according to the first aspect of the disclosure, the container comprising a chamber for storing the chain of pouches, the chamber comprising an opening providing user access to the chamber; and, a cover for covering the opening, and arranged so that in use the user may open the cover to access the chamber of the container through the opening.

According to a third aspect of the disclosure, there is provided a method of dispensing one or more pouches from a container containing a chain of pouches according to the first aspect of the disclosure, the method comprising: selecting a number of pouches from the chain of pouches to be removed from the container; removing said number of pouches from the chamber through an opening; and, separating said number of pouches from the chain of pouches.

According to a fourth aspect of the disclosure, there is provided an aerosol generating device comprising: a compartment configured to receive a plurality of pouches, wherein each pouch contains aerosolizable material and is porous to enable aerosol to flow through or out of the pouch; and, wherein the device is arranged to generate a flow of aerosol that flows through or from the pouches for inhalation by a user.

Further features and advantages of the disclosure will become apparent from the following description of preferred embodiments of the disclosure, given by way of example only, which is made with reference to the accompanying drawings.

DETAILED DESCRIPTION

Figure 1:
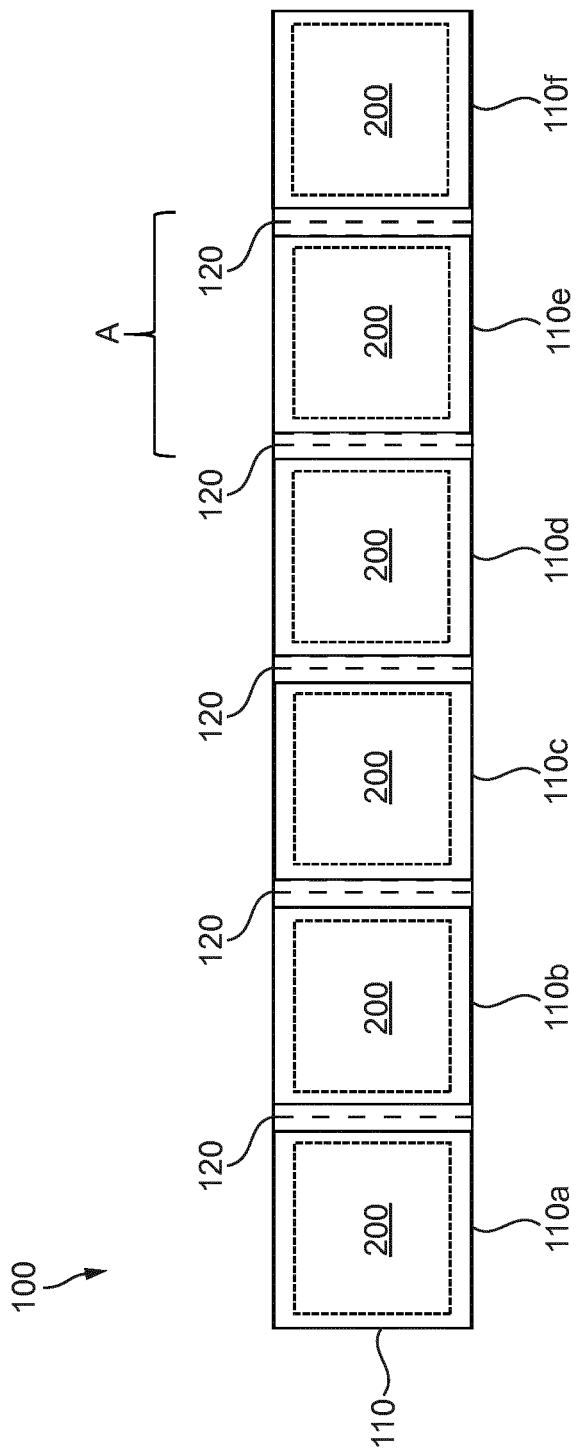
FIG. 1 shows a schematic plan view of a chain of pouches according to an example.

Referring to FIG. 1, an example of a schematic plan view of a chain 100 of pouches 110 is shown. The chain 100 contains a plurality of individual pouches 110 and each individual pouch 110 contains aerosolizable material 200. In use, one or more of the pouches 110 may be placed into a heating chamber of an aerosol generating device (not shown), for example, a Tobacco Heating Product device and heated so that a flow of aerosol is generated from the aerosolizable material 200 for inhalation by a user. Each of the pouches 110 is porous to enable aerosol to flow through or out of the pouch 110.

Advantageously, as each of the pouches 110 contains a set amount of aerosolizable material 200, it is relatively easy for a user to load a desired amount of aerosolizable material 200 into the heating chamber of the aerosol generating device (not shown). Furthermore, as the aerosolizable material 200 is contained within pouches 110, it can be loaded into the heating chamber in a relatively cleanly fashion.

The chain 100 has at least two pouches (110a,-110n) and in the example shown has 6 pouches 110 (110a,-110n).

The chain 100 has a respective weakened region 120 arranged between any two sequential pouches 110 in the chain 100. Each weakened region 120 allows a user to break the chain 100 at that weakened region 120 to remove one or more pouches 110 from the rest of the chain 100.

Each weakened region 120 may be, for example, any of a perforated region, a folded region or a scored region or any such region that facilitates a user separating two pouches (110a-110f) by breaking the chain 110 at that region 120.

The chain 100 may comprise any suitable material (or combination of materials) including any of: an aluminum mesh; filter material; food-grade plastic; silk; cellulose acetate; and, polylactic acid. The material may be any heat resistant material that is flexible. Each individual pouch 110 comprises the material of the chain 100 as a whole and the weakened regions 120 are formed in the material between the individual pouches (110a-110f).

Each pouch (110a-110f) preferentially does not create a thermal barrier between the aerosolizable material 200 and the external environment so that any heating of the pouch 110 efficiently heats the aerosolizable material 200. Each pouch 110 contains a quantity of aerosolizable material, e.g., up to about 250 mg of aerosolizable material. In an example, each pouch may contain from 0.1 to 250 mg of aerosolizable material 200. In other examples the pouch 110 contains from about 1 mg to 225 mg of aerosolizable material 200, or from about 5 mg to 200 mg, or from about 10 mg to about 100 mg.

Figure 2:
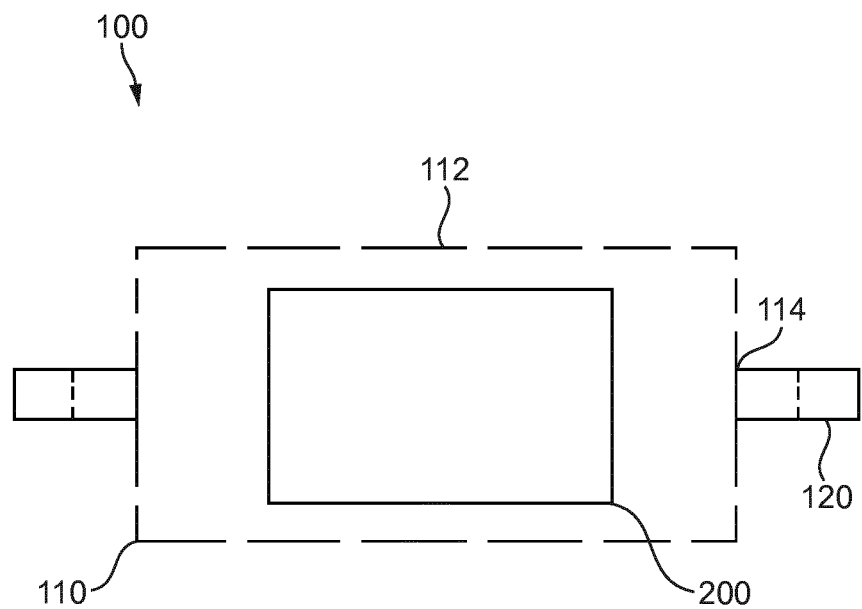
FIG. 2 shows a schematic side-on cross-sectional view of portion A of the chain of pouches of FIG. 1.

As best shown in FIG. 2 (which is a schematic side-on cross-sectional view of a portion of the chain 100 indicated as A in FIG. 1) each pouch 110 may comprise a plurality of pores 112 (or other such apertures) so as to make the pouch 110 porous. Each pouch 110 may, for example, have an average porosity such that a considerable airflow is enabled to pass through the pouch 110 but so that the aerosolizable material 200 is securely retained within the pouch 110. The area of the pores 112 of the pouch 110 may typically be around 0.03 to 1.5 mm$^2$, although the pore sizes may be up to 0.7 mm$^2$ or 1.1 mm$^2$.

In use, when a pouch or pouches 110 are heated in the heating chamber of a Tobacco Heating Product device or the like, the aerosolizable material 200 generates an aerosol which may flow out of or through a pouch 110 via the pores 112 of the pouch 110.

As is also illustrated in FIG. 2, each weakened region 120 may be arranged at around a mid-point on the height of the pouches 110 which it connects and may be attached to a pouch 110 by a join 114. In other examples, each weakened region 120 may be arranged along the full height or length of each pouch 110 to which it is connected. Preferentially each pouch 110 is robust enough, so that during its removal from the chain 100, the pouch 110 does not split or tear, as this might enable aerosolizable material 200 to exit the pouch 110. This may undesirably result in aerosolizable material 200 contacting the hands of a user.

Figure 3:
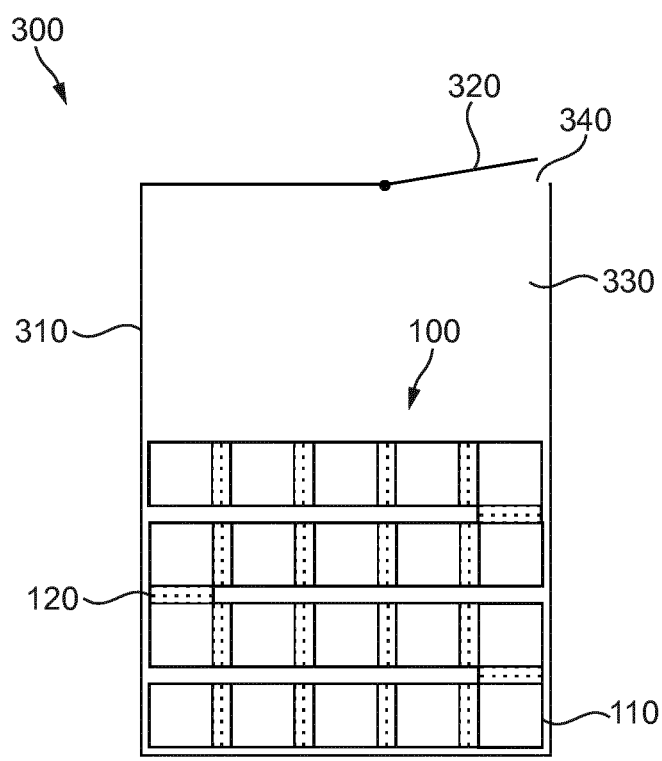
FIG. 3 shows a schematic side-on cross-sectional view of a container of a chain of pouches according to an example.

Referring now to FIG. 3, there is shown a schematic side-on cross-sectional view of a container 300 of a chain 100 of pouches 110 according to an example. The container 300 in the example shown contains a chain 100 of twenty pouches 110 linked by weakened regions 120. The chain 100 herein is shown to be folded back on itself, thereby saving space within the container 300 thereby increasing the number of pouches 110 that can be contained in the container 300. The container 300 has a container body 310 which at least in part defines the chamber 330 in which the chain 100 of pouches 110 is located. The container 300 also has a cover 320 for covering an opening 340 to the chamber 330. When the cover 320 is moved from covering the opening 340, a user may access the chamber 330 to e.g. remove or input a chain 100 of pouches 110 or remove or input a number of pouches 110 from a chain 100 of pouches 110.

In use, the user may move the cover 320 to reveal the opening 340. The user may then access the chamber 330 through the opening 340 and remove some of, or all of, the chain 100 of pouches 110 through the opening 340. The user may break off a number of pouches 110 from the chain 100 based on the desired user session and put the remaining pouches 110 in the chain 100 back into the container 300. The cover 320 may then be moved to cover the opening 340. The pouches 110 that have been removed from the chain 100 may then be placed into an aerosol generating device.

In an example, the container 300 may have features to assist in breaking the chain 100 of pouches 110 at weakened regions 120. The edge of the container body 310 near the opening 340 may have a serrated portion (not shown) for assisting in breaking the chain 100. Alternatively or additionally, the cover 320 may have a serrated portion for assisting in breaking the chain 100. The cover 320 and edge of the container body 310 near the opening 340, may together act like a jaw to assist in breaking the chain 100 as the cover 320 closes into contact with the container body 310. The user may therefore open the cover 320, pull out the chain 100 so that desired number of pouches 110 for the intended aerosol generating session pass through the opening 340 and then close the cover 320, to simultaneously break the chain 100, drop the remaining pouches 110 of the chain 100 back into the container 300, and cover the opening 340.

Figure 4:
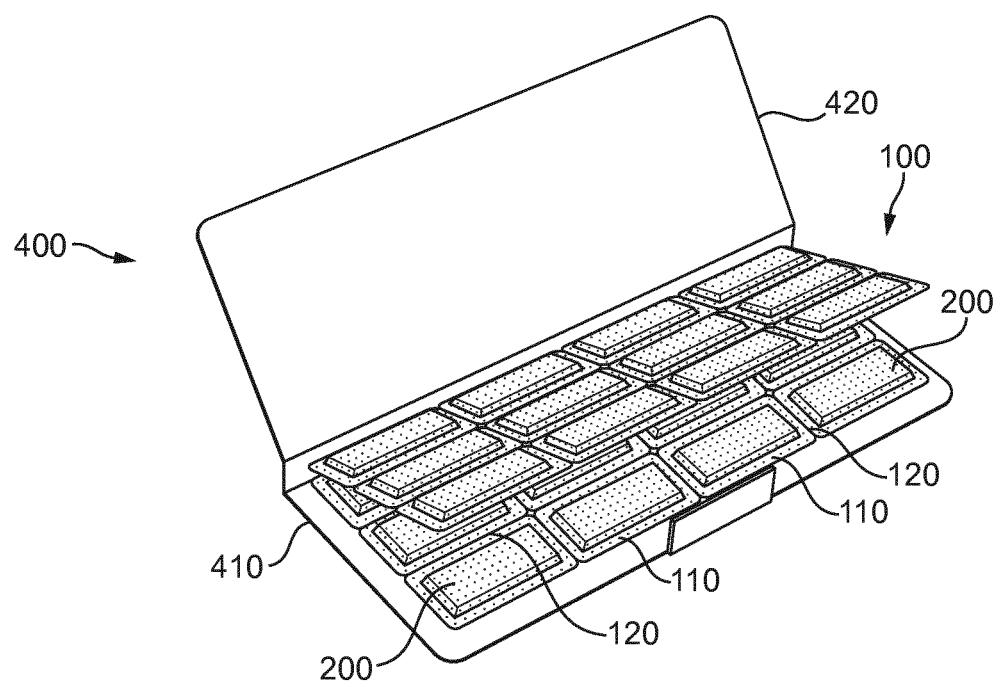
FIG. 4 shows a schematic perspective view of a container of a chain of pouches according to an example.

Referring now to FIG. 4, there is shown a schematic perspective view of a container 400 of a chain 100 of pouches 110 according to an example. The container 400 shown in FIG. 4 has a container body 410, and a cover 420 for covering an opening to the body 410 as in the example of a container shown in FIG. 3 and described above. The chain 100 of pouches 110 in the container 400 differs to the chain 100 of pouches 110 in FIG. 3. The chain 100 has a number of pouches 110 which are joined to other pouches 110 in the chain 100, by weakened regions 120, by end-to-end joins (as previously in FIG. 3) as well as by side-to-side joins. The chain 100 shown is made up of twelve pouches 110 in a three-rows-by-four-columns configuration such that each pouch 110 has at least two other pouches 110 connected to it by at least one end-to-end join and at least one side-to-side join. The pouches 110 in the second and third columns of the middle row will each be joined to four other pouches 110. The four other pouches 110 will be joined to the pouch 110 by four weakened regions 120 on both sides and on both ends of the pouch 100. The chain 100 of FIG. 4 is therefore joined together in more directions than the chains 100 of FIGS. 1 and 3. In total, the twelve pouches 120 are joined by seventeen weakened regions 120. The chain 100 arrangement can be seen to maximize the packing of the pouches 110 into the container 400 due to the size of the container 400.

In use, the chain 100 of FIG. 4 can be removed from the container 400 and a number of pouches 110 can be broken away from the chain 100 for insertion into an aerosol generating device. The pouches 110 may be broken in a line (in rows or columns for example) or as a clump from the chain 100 of FIG. 4, e.g. a two-by-two clump of four.

Figure 5:
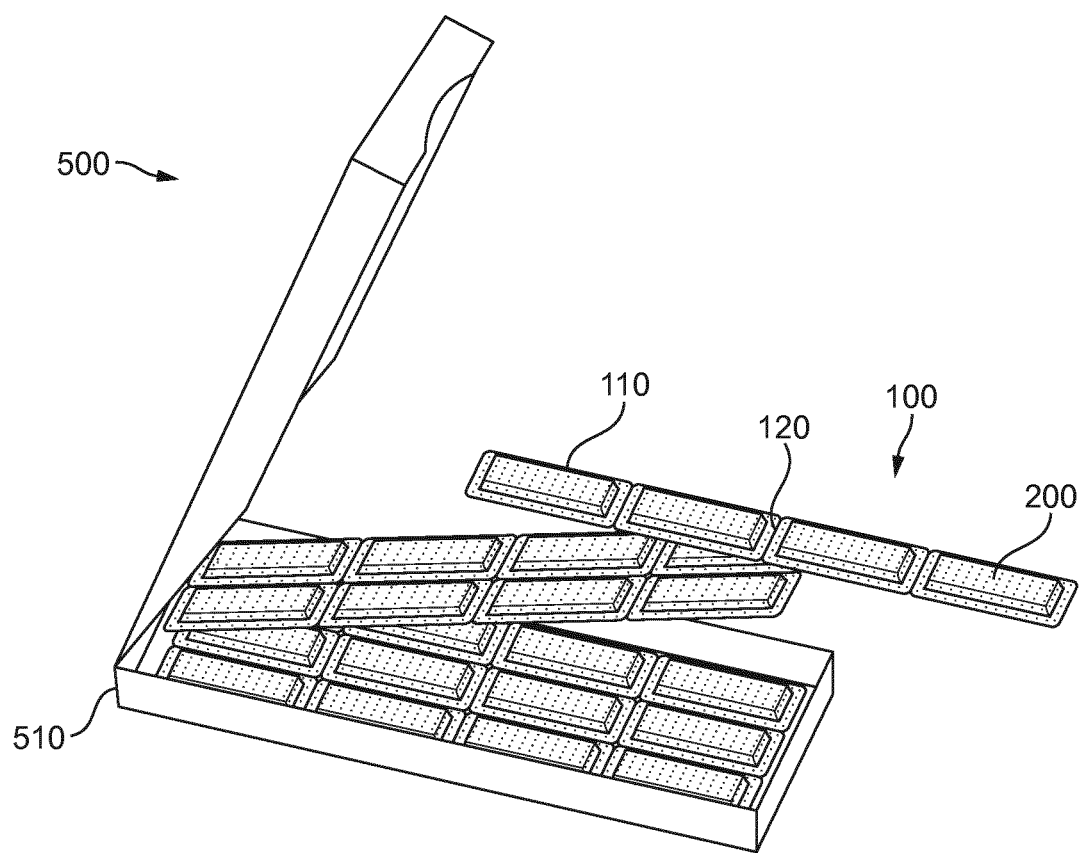
FIG. 5 shows a schematic perspective view of a container of a chain of pouches according to an example.

Referring now to FIG. 5, there is shown a schematic perspective view of a container 500 of a chain 100 of pouches 110 according to an example. The container 500 shown in FIG. 5 has a container body 510, and a cover 520 as in the examples of a container shown in FIG. 3 and FIG. 4 and described above. The chain 100 of pouches 110 in the container 500 differs in comparison to that in FIG. 3. The chain 100 has a number of pouches 110 which are joined to other pouches 110 in the chain 100, by weakened regions 120, by end-to-end joins as well as side-to-side joins. The chain 100 shown in FIG. 5 is the same as that described for FIG. 4 and so the description will not be repeated. In use, the cover 520 of the container 500 is removed to reveal the chain 100 of pouches 110. The chain 100 can then be removed from the container 500 and a number of pouches 110 removed from the chain 100. The pouches 110 may be broken in a line from the chain 100 as shown in FIG. 5 or as a clump. The chain 100 arrangement can be seen to maximize the packing of the pouches 110 into the container 500. The chain 100 may be folded back on itself to maximize packing in the container 500.

Figure 6:
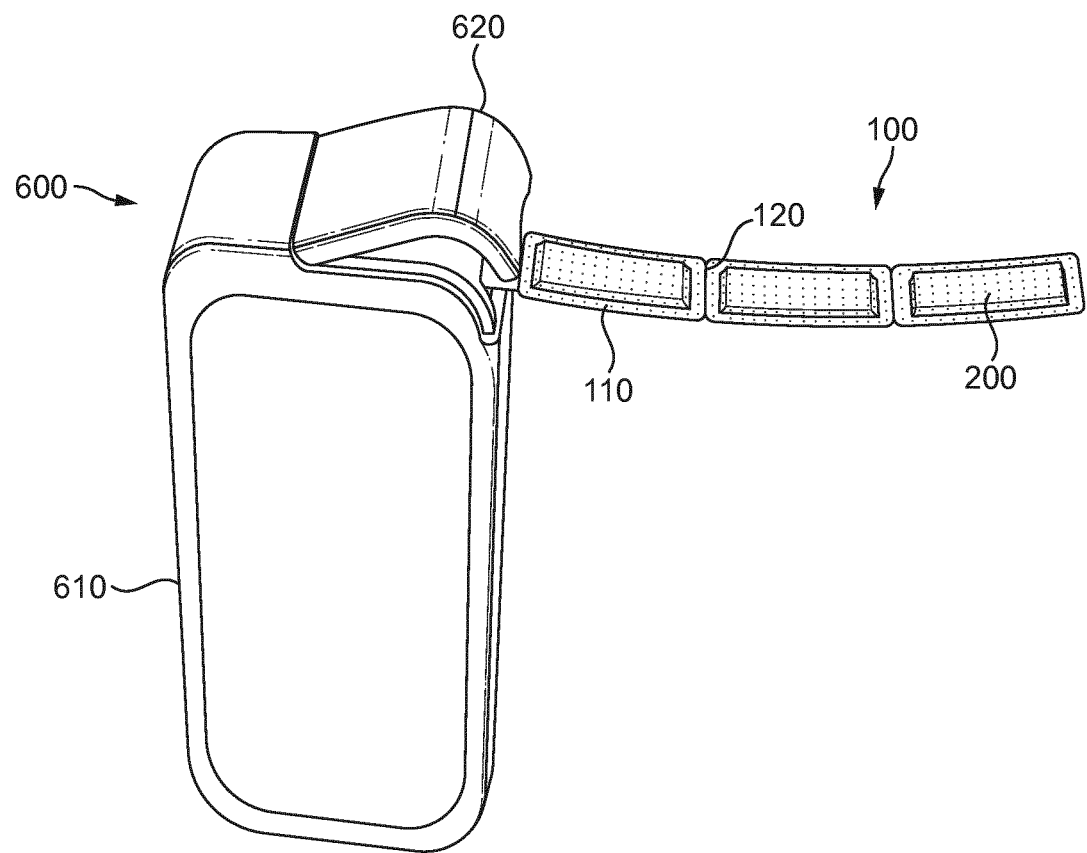
FIG. 6 shows a schematic perspective view of a container of a chain of pouches according to an example.

Referring now to FIG. 6, there is shown a schematic perspective view of a container 600 of a chain 100 of pouches 110 according to an example. The container 600 shown in FIG. 6 has a container body 610, and a cover 620 for covering an opening to the container body 610 as in the examples of a container shown in FIGS. 3, 4 and 5 and described above. The chain 100 of pouches 110 in the container 600 differs in comparison to those in FIGS. 4 and 5 but is similar to that shown in FIG. 1. The chain 100 has a number of pouches 110 which are joined, by weakened regions 120, end-to-end only to other pouches 110 in the chain 100. The chain 100 shown in FIG. 6 is the same as that described for FIG. 1 and so the description will not be repeated. In use, the cover 620 of the container 600 is removed to reveal the chain 100 of pouches 110. The chain 100 can then be removed from the container 600 and a number of pouches 110 removed from the chain 100. The pouches 110 may be removed from the chain 100 by hand or by closing the cover 620 onto a weakened region 120 as described above. The chain 100 may be folded back onto itself within the container 610 so as to maximize the packing of the pouches 110 within the container 600.

Figure 7:
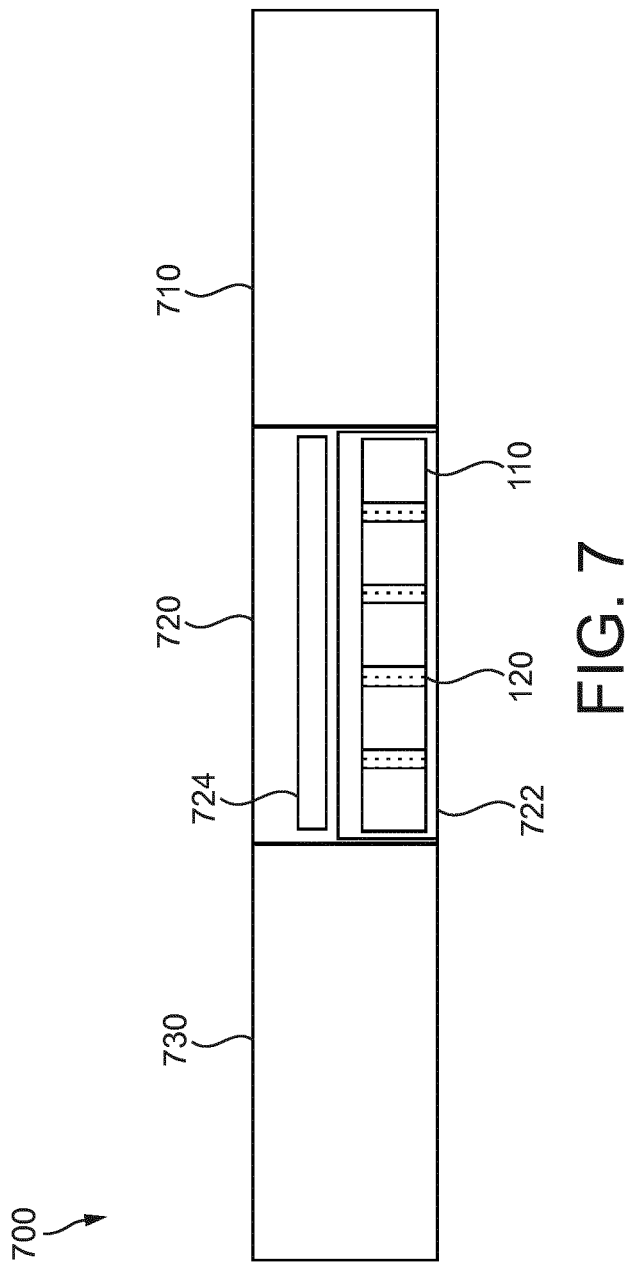
FIG. 7 shows a longitudinal cross-sectional view of an aerosol generating device according to an example.

Referring now to FIG. 7, there is shown an aerosol generating device 700. The aerosol generating device 700 has a power unit 710, a heating chamber 720 and a mouthpiece 730. The power unit 710 may contain batteries and power circuitry and the like. The heating chamber 720 may contain one or more heaters 724, associated circuitry, and one or more compartments 722 for containing aerosol generating material or aerosolizable material 200. The mouthpiece 730 may contain air flow passages and the like such that aerosol generated within the device 700 may exit the device 700 and be inhaled by a user. The device 700 also has air inlets (not shown) so that air from the environment exterior to the device 700 may pass into the device 700 during use.

The heating chamber 720 in the example shown has a removable compartment 722. The removable compartment 722 may be removed from the heating chamber 720 and one or more pouches 110 taken from a chain 100 of pouches 110 may be inserted into the compartment 722. In use, a number of pouches 110 based on the desired aerosol generating session may be inserted into the compartment 722. The compartment 722 may be sized so that a specific maximum number of pouches 110 suitable for a lengthy user session can be inserted into the compartment 722. That is, the compartment 722 is sized so as to be able to receive a plurality of pouches 110. The pouches 110 may be joined to one another and may be folded prior to insertion into the compartment 422 or be folded during insertion into the compartment 722 so that the pouches 110 occupy less space within the compartment 722. The folding may occur along the weakened regions 120. Alternatively, each pouch may be separated from one another with the separated pouches subsequently being inserted into the compartment 722.

After insertion of the pouches 110 into the compartment 722, the compartment 722 may be inserted back into the heating chamber 720. The compartment 722 may be arranged close to heater 724 in the heating chamber 720 so that the heater 724 can directly heat the compartment 722 and therefore the pouches 110 within the compartment 722 and therefore the aerosolizable material 200 within the pouches 110. Alternatively, the heater 724 may heat air flow prior to the air flow passing into the compartment 722 and through the porous pouches 110. The hot air flow may entrain flavorants from the aerosolizable material 200 prior to exiting the compartment 722 towards the mouthpiece 730 for inhalation by a user. In another example, the heater 724 may heat aerosol generating material such as an e-liquid or the like, and the aerosol may be passed through the compartment 722, through the porous pouches 110 to entrain flavorants from the aerosolizable material 200 prior to exiting the compartment 722 towards the mouthpiece 430 for inhalation by a user.

In an example, the compartment 722 may be replaced with a removable cover or a slidable cover or window (not shown) and a storage area (not shown). The cover or window can be moved to provide an entrance to the storage area for the pouches 110. This storage area may act in the same way as the compartment 722 as described above, but without being removable from the device 700. After the pouches 110 are inserted into the storage area, the cover or window may be closed. An airtight seal would be required for the compartment 722 or the cover or window of the storage area to prevent aerosol exiting the device 700 not at the mouthpiece 730.

Figure 8A:
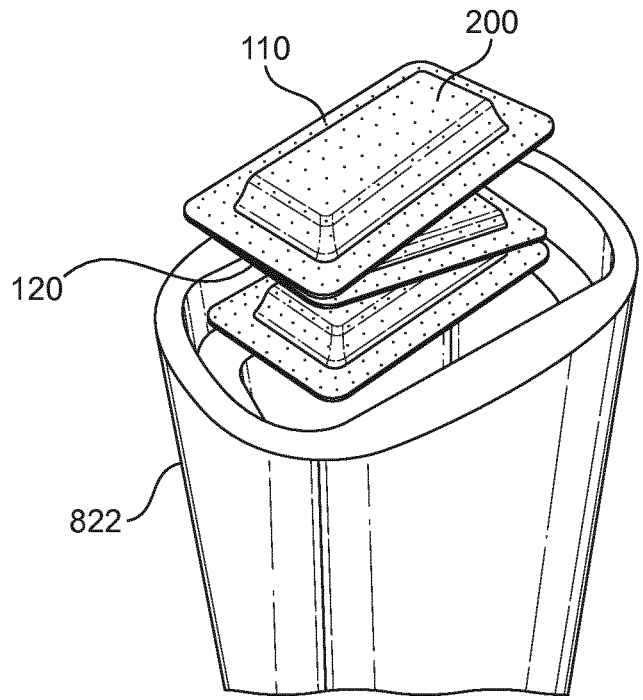
FIGS. 8a and 8b show a schematic perspective view of a compartment of an aerosol generating device according to an example.
Figure 8B:
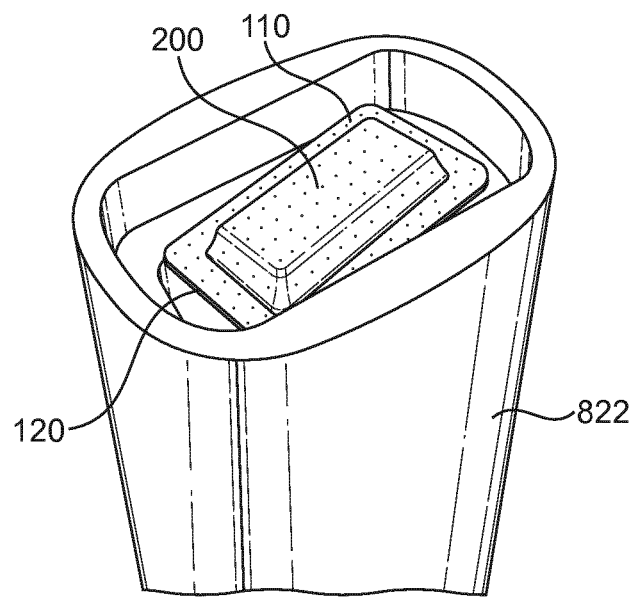

Referring now to FIGS. 8a and 8b, there is shown a schematic perspective view of a compartment 822 for an aerosol generating device according to an example. The compartment 822 in use is removed from an aerosol generating device, like that shown in FIG. 7, has a number of pouches 110 inserted into it and is then re-attached to the aerosol generating device. The compartment 822 shown in FIGS. 8a and 8b is sized so that is has a cross-sectional area suitable for housing one pouch 110. In this example, when a number of pouches 110 is desired to be input into the compartment 822, the pouches 110 may be folded along the weakened regions 120 connecting the pouches 110 to optimize the space occupied in the compartment 822 by the pouches 110. This folding along weakened region 120 can be clearly seen in FIG. 8a.

The chain 100 of pouches 110 may contain a number of pouches 110 in the chain 100. Certain pouches 110 on the chain 100 may differ to other pouches 110 on the chain 100. For example, some pouches 110 may contain a first type of aerosolizable material 200 whereas other pouches 110 may contain other types of aerosolizable material 200. Some pouches 110 may have a certain average porosity whereas other pouches 110 may have a different average porosity. Differences in average porosity may lead to pouches 110 with higher porosity emitting aerosol earlier in a user session than pouches 110 with a lower porosity. Certain pouches 110 may be formed from a more thermally conductive material than other pouches 110 so as to provide aerosol earlier in the user session than the other pouches 110. These variations may enable a session profile to be selected by a user for a specific user session based on the pouches 110 selected for that session.

As used herein, the term "aerosol generating material" and "aerosolizable material" refers to material that provides volatilized components upon heating in the form of an aerosol. In some embodiments, the aerosol generating material may comprise a tobacco component, wherein tobacco component is any material comprising tobacco or derivatives thereof. The tobacco component may comprise one or more of ground tobacco, tobacco fiber, cut tobacco, extruded tobacco, tobacco stem, reconstituted tobacco and/or tobacco extract. Other types of aerosolizable may include leaf material, herbal material or organoleptic substances as used in aromatherapy and the like. In some embodiments, the aerosol-generating substrate may comprise a tobacco substitute.

As used herein, the terms "flavor" and "flavorant" refer to materials which, where local regulations permit, may be used to create a desired taste or aroma in a product for adult consumers. They may include extracts (e.g., licorice, hydrangea, Japanese white bark magnolia leaf, chamomile, fenugreek, clove, menthol, Japanese mint, aniseed, cinnamon, herb, wintergreen, cherry, berry, peach, apple, Drambuie, bourbon, scotch, whiskey, spearmint, peppermint, lavender, cardamom, celery, cascarilla, nutmeg, sandalwood, bergamot, geranium, honey essence, rose oil, vanilla, lemon oil, orange oil, cassia, caraway, cognac, jasmine, ylang-ylang, sage, fennel, piment, ginger, anise, coriander, coffee, or a mint oil from any species of the genus Mentha), flavor enhancers, bitterness receptor site blockers, sensorial receptor site activators or stimulators, sugars and/or sugar substitutes (e.g., sucralose, acesulfame potassium, aspartame, saccharine, cyclamates, lactose, sucrose, glucose, fructose, sorbitol, or mannitol), and other additives such as charcoal, chlorophyll, minerals, botanicals, or breath freshening agents. They may be imitation, synthetic or natural ingredients or blends thereof. They may be in any suitable form, for example, oil, liquid, solid, or powder. For example, a liquid, oil, or other such fluid flavorant may be impregnated in a porous solid material so as to impart flavor and/or other properties to that porous solid material. As such, the liquid or oil is a constituent of the solid material in which it is impregnated.

The above embodiments are to be understood as illustrative examples of the disclosure. Further embodiments of the disclosure are envisaged. It is to be understood that any feature described in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the invention, which is defined in the accompanying claims.

The invention claimed is:

1. A chain of pouches comprising:
a plurality of pouches, each pouch of the plurality of pouches containing an aerosolizable material,
wherein each pouch in the chain of pouches is connected to at least one other pouch in the chain of pouches by a respective weakened region, wherein the chain of pouches is arranged to be foldable and breakable at each respective weakened region, and wherein each pouch is porous and comprises a plurality of pores to enable aerosol to flow through or out of the pouch, wherein the average area of each pore is 0.03 mm$^2$ to 0.15 mm$^2$.

2. The chain of pouches according to claim 1, wherein each pouch is made from at least one of: an aluminum mesh, a filter material, a food-grade plastic, silk cellulose acetate, or polyactic acid, or
each pouch contains at least about 0.1 mg to 250 mg of the aerosolizable material.

3. The chain of pouches according to claim 1, wherein at least one of the weakened regions is a perforated region or a folded region.

4. The chain of pouches according to claim 1, wherein the aerosolizable material is at least one of the following: tobacco; a tobacco-containing material; leaf material; herbal material; or a substance as used in aromatherapy.

5. A container for containing a chain of pouches according to claim 1, the container comprising:
a chamber for storing the chain of pouches, the chamber comprising an opening providing user access to the chamber;
a cover for covering the opening, arranged so that in use a user may open the cover to access the chamber of the container through the opening; and
a container body,
the chamber being defined at least in part by the container body, wherein the container body and the cover cooperate to form a jaw for breaking the chain of pouches.

6. The container according to claim 5, further comprising a serrated portion for piercing the chain of pouches, and wherein either:
the container body comprises the serrated portion and the serrated portion is arranged near the opening to the chamber, or
the cover comprises the serrated portion.

7. The container according to claim 5, wherein the container contains a chain of pouches of at least two pouches.

8. A method of dispensing one or more pouches from a container containing the chain of pouches according to claim 1, the method comprising:
selecting a number of pouches from the chain of pouches to be removed from the container;
removing the number of pouches from the chamber through an opening;
separating the number of pouches from the chain of pouches; and
moving a cover that covers the opening to the chamber subsequent to removing the number of pouches from the chamber through the opening.

9. The method of dispensing according to claim 8, wherein separating the number of pouches from the chain of pouches comprises one of:
breaking the chain of pouches at a weakened region, or
cutting the chain of pouches using a serrated portion of the container.

10. The method according to claim 8, comprising:
inserting the number of pouches into a compartment of an aerosol generating device.

11. An aerosol generating device comprising:
a compartment configured to receive a plurality of pouches, wherein each pouch of the plurality of pouches contains an aerosolizable material and is porous to enable aerosol to flow through or out of the pouch;
wherein the aerosol generating device is arranged to generate a flow of aerosol that flows through or from the plurality of pouches for inhalation by a user, wherein the compartment is configured to receive a chain of pouches comprising a plurality of pouches, each pouch of the plurality of pouches containing an aerosolizable material, wherein each pouch in the chain of pouches is connected to at least one other pouch in the chain of pouches by a respective weakened region, wherein the chain of pouches is arranged to be foldable and breakable at each respective weakened region, and wherein each pouch is porous and comprises a plurality of pores to enable aerosol to flow through or out of the pouch, wherein the average area of each pore is 0.03 $mm^2$ to 0.15 $mm^2$.

12. The aerosol generating device according to claim 11, wherein at least one of:

the compartment is removably connectable to the aerosol generating device, or the compartment comprises an opening through which a chain of pouches may be inserted into the compartment.

13. The aerosol generating device according to claim 11, further comprising circuitry arranged to prevent operation of the aerosol generating device when the compartment is not connected to the aerosol generating device.

* * * * *